United States Patent [19]

Wagman et al.

[11] Patent Number: 4,777,037

[45] Date of Patent: Oct. 11, 1988

[54] HAIR CONDITIONING COMPOSITIONS CONTAINING VOLATILE CYCLIC SILICONE AND QUATERNARY NITROGEN-CONTAINING AGENT

[75] Inventors: Julius Wagman; Dale H. Johnson, both of Chicago, Ill.

[73] Assignee: Helene Curtis Industries, Inc., Chicago, Ill.

[21] Appl. No.: 503,573

[22] Filed: Jun. 13, 1983

Related U.S. Application Data

[63] Continuation-in-part of Ser. No. 286,877, Jul. 29, 1981, abandoned.

[51] Int. Cl.[4] .......................... A61K 7/06; A61K 7/09; A61K 7/11
[52] U.S. Cl. ........................................ 424/70; 424/71; 424/72
[58] Field of Search .............................. 424/70, 71, 72

[56] References Cited

U.S. PATENT DOCUMENTS

| 3,208,911 | 9/1965 | Oppliger | 424/70 |
| 3,392,040 | 7/1968 | Kass | 424/70 |
| 3,957,970 | 5/1976 | Korkis | 424/70 |
| 3,993,744 | 11/1976 | Cella et al. | 424/70 |
| 4,185,087 | 1/1980 | Morlino | 424/70 |
| 4,275,055 | 6/1981 | Nachtigal et al. | 424/70 |
| 4,374,825 | 2/1983 | Bolich, Jr. et al. | 424/70 |
| 4,387,090 | 6/1983 | Bolich, Jr. | 424/70 |

FOREIGN PATENT DOCUMENTS

| 0072095 | 6/1981 | Japan | 424/70 |
| 57-50909 | 3/1982 | Japan . | |

Primary Examiner—Albert T. Meyers
Assistant Examiner—Freda L. Krosnick
Attorney, Agent, or Firm—Dressler, Goldsmith, Shore, Sutker & Milnamow, Ltd.

[57] ABSTRACT

Hair conditioning emulsions providing improved detangling and combing ease and a creamy feel on wet hair are disclosed. The compositions contain water, a certain quaternary nitrogen-containing conditioning agent and about 1 to 4 weight percent polydimethyl cyclosiloxane having an atmospheric boiling point of from about 150° C. to about 250° C.

20 Claims, No Drawings

HAIR CONDITIONING COMPOSITIONS CONTAINING VOLATILE CYCLIC SILICONE AND QUATERNARY NITROGEN-CONTAINING AGENT

CROSS REFERENCE TO RELATED APPLICATION

This is a continuation-in-part of application Ser. No. 286,877, filed July 29, 1981, now abandoned.

TECHNICAL FIELD

The present invention relates to hair conditioning compositions, and more particularly to aqueous hair conditioners which contain a volatile cyclic silicone and a member of a specific class of quaternary nitrogen conditioning agents that provide improved combing properties.

BACKGROUND ART

Hair conditioning compositions, including creme rinses, are well known in the art for improving combing ease for wet and dry hair. These compositions are typically aqueous emulsions which contain a quaternary amine compound as the principal conditioning agent. The quaternary nitrogen-containing compound can be a polymeric material having a plurality of quaternary nitrogen atoms per molecule or a molecule having at least one long carbon atom chain and an average of one quaternary nitrogen atom per molecule.

U.S. Pat. No. 3,933,744 to Cella et al. discloses that cationic compounds, such as quaternary nitrogen-containing compounds, and silicones can be utilized in conjunction with perfluorinated compounds in hair treatment compositions. The silicones specifically disclosed by Cella et al. are poolyoxyethylene poly methylsiloxanes which are presumed to be water-soluble or dispersible. Both the quaternary nitrogen-containing compounds and silicones disclosed are utilized in relatively small amounts, e.g., at about 0.05 weight percent of the composition.

British Pat. No. 1,598,567 discloses the use of volatile silicones having a boiling point in the range 99° to 265° C. along with a water-soluble or water-dispersible fluoresurfactant (sic) in hair conditioning compositions. Both linear and cyclic dimethyl polysiloxanes are disclosed as being useful, with cyclic compounds having four or five dimethyl siloxy units being preferred. The use of the fluoresurfactant is said to avoid the formation of an oleophilic hair surface as is said to occur with the use of quaternary nitrogen-containing conditioning agents.

South African patent application No. 666421 teaches the use of compositions containing straight chain and volatile cyclic silicone fluids as providing gloss and conditioning effects to hair dressings. Use of the silicone fluid is illustrated dissolved in a solvent or in an aqueous emulsion containing non-ionic surfactants as emulsifying agents.

High molecular weight silicones having viscosities greater than about 100 centistokes at 25° C. are also known to provide lubricity or sheen to various cosmetic preparations. This is shown in U.S. Pat. Nos. 2,942,008, No. 3,594,409, No. 3,824,303 and No. 4,014,995.

None of this art specifically teaches or suggests that low molecular weight, low viscosity, cyclic volatile silicones combined in water with a member of a specific class of cationic compounds would provide improved combing to hair or creaminess when used as hair conditioning compositions.

SUMMARY OF THE INVENTION

An improved hair conditioning composition is disclosed which contains water, a quaternary nitrogen-containing conditioning agent containing (a) two long aliphatic chains each having about 12 to about 18 carbon atoms and (b) two identical or different short chain alkyl groups having one or two carbon atoms each and a polydimethyl cyclosiloxane having an atmospheric boiling point of about 150° C. to about 250° C. A useful hair conditioning composition is formed between the above two ingredients when the quaternary nitrogen-containing conditioning agent is present at about 0.5 to about 5 weight percent of the composition and the volatile cyclic silicone is present at about 1 to about 4 weight percent of the composition.

A particularly preferred hair conditioning composition is an aqueous emulsion which includes about 1 to about 4 percent polydimethyl cyclosiloxane having an atmospheric boiling point of from about 150° C. to about 250° C., about 0.5 to about 5 percent of the above quaternary nitrogen-containing conditioning agent, about 0.5 to about 10 percent of a long chain fatty alcohol having about 11 to about 18 carbon atoms in its fatty chain, and about 0.1 to about .2 percent of a tertiary amidoamine; all of the percentages being based upon the total weight of the composition. The tertiary amidoamine is a compound having a structure conforming to the formula $R^1—C(=O)—NH—R^2—N(R^3)_2$ wherein $R^1$ is a fatty chain having about 11 to about 17 carbon atoms, $R_2$ is an alkylene group having 2 or 3 carbon atoms and each $R_3$ is ethyl or methyl.

It was unexpected that the combination of low viscosity, low molecular weight, volatile cyclic silicone and the quaternary nitrogen-containing conditioning agent useful herein would provide either the improved overall combing or the creamy on-hair feel that are provided by the conditioning compositions of this invention. This finding was unexpected since both a very volatile silicone having a boiling point of about 100° C. and a high molecular weight, non-volatile silicone when combined with a useful quaternary nitrogen-containing conditioning agent provided the hair with an oily feel and poorer overall combing properties. A further unexpected finding was that conditioning compositions prepared from the volatile cyclic silicone and quaternary nitrogen-containing compound of this invention provided combing that was better than the combing provided by the same cyclic silicone and other typical quaternary nitrogen-containing conditioning agents used in amounts comparable to those of the useful quaternary nitrogen-containing conditioning agents.

DISCLOSURE OF THE INVENTION

The present invention relates to improved hair conditioning compositions which contain water and a combination of a volatile cyclic silicone and a quaternary nitrogen-containing conditioning agent. The compositions of this invention are useful both as aqueous dispersions and as aqueous emulsions. The aqueous emulsions are preferably stable emulsions in which water comprises the external phase, although compositions containing phases which separate after standing for more than about one hour are also useful herein.

The volatile silicones utilized in this invention are water-insoluble cyclic compounds having an average of about 3 to about 6-[O—Si(CH$_3$)$_2$]— repeating group units per molecule and boil at atmospheric pressure at from about 150° C. to about 250° C. The polydimethyl cyclosiloxanes having an average of about 4 to about 5 repeating units per molecule, the tetramer and pentamer, are particularly preferred.

The particularly preferred polydimethyl cyclosiloxanes have boiling points at ambient pressures in the range of about 170° C. to about 220° C., and viscosities at 25° C. of from about 2 to about 6 centistokes. These materials are commercially available under the designations Silicon SF-1173 and Silicone SF-1202 from General Electric, and Silicone 344 Fluid and Silicone 345 Fluid from Dow Corning Corporation, the tetramer being listed first in each instance.

Volatile silicones are preferably present in the hair conditioning compositions of this invention at from about 1 to about 4 weight percent of the composition. More preferably, these polydimethyl cyclosiloxanes are present at from about 1.5 to about 3 percent by weight of the conditioning composition.

Volatile silicones are said by one manufacturer to be useful in various cosmetic compositions such as antiperspirants, deodorants, hari sprays, hair coloring and hair grooming products, powder and color products and stick products, and because of their low viscosity and surface tension provide a light silky feel on hair and skin. These silicones, and a very volatile silicone (hexamethyl disiloxane, boiling point =100° C.) are also reported to be non-greasy but to provide subtle lubrication. It has been unrecognized in the hair conditioning arts that the before-described volatile cyclic silicones, used in the amounts described, along with the hereafter discussed cationic compounds would provide the overall combing benefits which are observed herein.

In addition to water, which typically constitutes at least about 80 weight percent of the weight of the conditioning composition, and more preferably about 90 weight percent, and the volatile cyclic silicone, the compositions of this invention also contain at least a water-soluble or water-dispersible quaternary nitrogen-containing conditioning agent that is also sometimes referred to herein as a cationic compound. A long chain fatty alcohol is also present in more preferred compositions, and a tertiary amidoamine is additionally present in particularly preferred compositions.

The quaternary nitrogen-containing conditioning agents are preferably present at from about 0.5 to about 5 percent by weight of the composition as an active ingredient. More preferably, the quaternary nitrogen-containing conditioning agent is present at from about 2 to about 3 weight percent, as an active ingredient.

The class of quaternary nitrogen-containing conditioning agents useful herein contain one quaternary nitrogen atom having (a) two long aliphatic chains and (b) two identical or different short chain alkyl groups having one or two carbon atoms, each bonded to the quaternary nitrogen atom. The two long chains each contain about 12 to about 18 carbon atoms.

Illustrative conditioning agents include distearyldimethylammonium chloride and dilauryldimethylammonium chloride. These compounds are named Quaternium-5 and Quaternium-47, respectively, in the *CTFA Cosmetic Ingredient Dictionary*, 2nd ed., 1977, published by the Cosmetic, Toiletry and Fragrance Association, Inc., hereinafter referred to as the *CTFA Dictionary*.

It is noted that the long aliphatic chain of the beforementioned conditioning agents need not be solely or primarily of one chain length, i.e., the long chain need not be cetyl, myristyl, lauryl or stearyl. Rather, conditioning agents whose long aliphatic chain contains a mixture of lengths can be used. Such conditioning agents are conveniently prepared from naturally occurring materials, such as tallow, coconut oil, soya oil and the like, or from synthetically produced mixtures. Examples of useful conditioning agents having mixed aliphatic chain lengths include dimethyldi-(hydrogenated tallow)ammonium chloride and dialkyldimethylammonium chloride wherein each alkyl group is a saturated group consisting primarily of 16 carbon atoms. These quaternary nitrogen-containing conditioning agents are named Quaternium-18 and Quaternium-31, respectively, in the *CTFA Dictionary*.

The compositions of this invention containing only water, volatile cyclic silicone and quaternary nitrogen-containing conditioning agent are milky-white, relatively viscous dispersions. Those compositions are stable to phase separation at a temperature of about 20° to about 25° C. for a period of time of at least 24 hours after their preparation, and are typically stable to phase separation indefinitely at such temperatures.

The compositions of this invention can also be in the form of emulsions that contain additional amounts of hydrophilic and/or hydrophobic ingredients. Emulsions containing additional hydrophobic materials are particularly preferred. It is preferred that those emulsions be stable to phase separation at a temperature of about 25° C. for a period of about 24 hours after their preparation. The emulsions are more preferably stable to phase separation at temperature normally found in commercial product storage and shipping for periods of one year or more.

Long chain fatty alcohols having from about 11 to about 18 carbon atoms in the long fatty chain can be constituents of the conditioning emulsions of this invention. These alcohols can be used alone, or in admixture with each other. When included in the compositions, the alcohol is preferably present at from about 0.5 to about 10 weight percent of the composition, and more preferably at from about 2 to about 5 weight percent.

Lauryl alcohol, oleyl alcohol, myristyl alcohol, stearyl alcohol, and the like, and mixtures thereof are contemplated herein. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having *CTFA Dictionary* names of Ceteth-1 and Steareth-2, respectively.

A tertiary amidoamine can also be present in the hair conditioning compositions of this invention, and is present in particularly preferred compositions at a concentration of from about 0.1 to about 2 weight percent of the composition, and more preferably at from about 0.25 to about 1 weight percent.

The tertiary amidoamines useful herein have structures conforming to the formula $R^1$—C(=O)—NH—$R^2$—N($R^3$)$_2$ wherein $R^1$ is a fatty chain having about 11 to about 17 carbon atoms, $R^2$ is an alkylene group having 2 or 3 carbon atoms and each $R^3$ is ethyl or methyl. Exemplary, useful, tertiary amidoamines include dimethylaminopropyl stearmide, diethylaminoethyl stearamide and dimethylaminopropyl myristamide. The $R^1$ group of the tertiary amidoamines can also be prepared from materials having differing chain lengths, and thus the $R^1$ group can be prepared from coconut, soya and tallow fatty acids, or the like.

The hair conditioning compositions of this invention suitably are near neutral to slightly acidic in pH value. Thus, the hair conditioners of this invention preferably have pH values of from about 4 to about 8, and more preferably from about 5.5 to about 6.5.

Ingredients in addition to water and the previously discussed ingredients can also be present in the composition of this invention. These additional ingredients include, but are not limited to, polyhydric alcohols, such as propylene glycol or glycerin, hydroxyethylated fatty alcohols having from about 12 to 18 carbon atoms in the fatty chain and an average of about 15 to about 30 moles of ethylene oxide added per mole of alcohol, inorganic salts such as sodium or potassium chlorides, perfume, colorants, preservatives and the like. Suitable hydroxyethylated fatty alcohols include the previously described fatty alcohols having from about 11 to 18 carbon atoms which contain the desired amount of hydroxyethylation such as polyoxyethylene (20) cetyl ether, polyoxyethylene (30) stearyl ether, polyoxyethylene (15) lauryl ether, the polyoxyethylene glycol ether of synethic fatty alcohols having about 11 to 15 carbons in the fatty chain and an average of 20 moles of ethylene oxide per mole of alcohol, and the polyethylene glycol ether of fatty alcohols containing primarily cetyl and stearyl alcohol and an average of 20 moles of ethylene oxide per mole of alcohol. These exemplary hydroxyethylated fatty alcohols are given the following *CTFA Dictionary* names, respectively: Ceteth-20, Steareth-30, Laureth-15, Pareth-15-20 and Ceteareth-20.

It is believed that the volatile cyclic silicone and useful quaternary nitrogen-containing conditioning agent interact to form a complex of some kind in water. The evidence indicating the formation of a complex is presented in the following Examples and includes data from conductivity and nuclear magnetic resonance studies, as well as data generated from combing hair tresses mechanically and from observation of compositional stability.

The data from the conductivity studies indicate that the useful quaternary nitrogen-containing conditioning agents have lower conductivities and are therefore less mobile or more weakly dissociated in water than are typical quaternary nitrogen-containing agents that are not useful herein. Those data also show that addition of a volatile cyclic silicone in the required amount provides an increase in conductivity for the useful cationic compound with the maximum effect occurring at a molar ratio of silicone to cationic compound of about 0.5:1 to about 2:1. The addition of a similar amount of the same silicone to an aqueous solution of a non-useful cationic conditioner has little effect upon the conductivity, generally causing a slight decrease in conductivity.

The compositions containing the ingredients of this invention that appear to form a complex in water also provide wet combing on normal and bleached/waved hair that is superior to the wet combing provided by a volatile cyclic silicone and a non-useful quaternary nitrogen-containing conditioning agent. That wet combing superiority was demonstrated at a confidence level of at least 97.5 percent on bleached/waved hair, and at least 90 percent for normal hair.

The data of the Examples also show that particularly preferred compositions of this invention provided better combing that did similar compositions containing no silicone of any kind, a high molecular weight, non-volatile silicone instead of the volatile cyclic silicone or a straight chain low molecular weight volatile silicone. The data further show a substantial, about 30 percent for the studied conditions, improvement in combing when hair was treated with a composition of this invention containing water, volatile cyclic silicone and quaternary nitrogen-containing conditioning agent as compared to a similar solution that contained no volatile cyclic silicone.

The fact that compositions containing water, a volatile cyclic silicone and the selected quaternary nitrogen-containing conditioning agent were stable to separation after about 24 hours at room temperature, while similar compositions containing the same amount of non-useful cationic conditioners separated during that period also lends support to the theory of complex formation or some other interaction between the particular ingredients of this invention.

Thus, the improvement obtained in combining the components of the compositions of this invention is not a mere aggregate of the expected properties contributed by each of the volatile cyclic silicone and quaternary nitrogen-containing conditioning agent. Rather, the combination of the two ingredients in the before-stated amounts provide combing; i.e., conditioning, properties in excess of what would be expected from a summation of the combing effects of the individual ingredients. That combination also provides a creaminess to the particularly preferred compositions that is unexpected. The combing effects being greater than the expected sum of effects from each of the ingredients and added creaminess also lend support to the hypothesis that a complex is formed in water. It is noted that since the volatile cyclic silicones are insoluble in water, and form a separate phase on the surface of water, the isolated combing effects due to the volatile cyclic silcone alone cannot be measured.

The data from the various determinations in the Examples tend to indicate the existance of a complex formed between the volatile cyclic silicone and the useful quaternary nitrogen-containing conditioning agent. The existence of a complex is proposed as a means for explaining the extraordinary results obtained using the compositions of this invention. However, applicant does not wish to be bound by any theory or hypothesis as to the mechanism by which the compositions of this invention actually obtain their unusual, and unexpected results.

The invention is further illustrated by the Examples which follow.

EXAMPLE 1

Hair Conditioning Emulsion A

A particularly preferred hair conditioning composition according to this invention was prepared having the ingredients and amounts listed below.

|     | Ingredient | Amounts (Weight percent) |
| --- | --- | --- |
| (1) | Quaternium-31[1] (68% active) | 3.3 |
| (2) | Cetyl alcohol | 3.25 |
| (3) | Volatile cyclic silicone[2] | 2.0 |
| (4) | Promulgen G[3] | 1.0 |
| (5) | Dimethylaminopropyl stearamide | 0.5 |
| (6) | Propylene glycol | 0.5 |
| (7) | Perfume | 0.4 |
| (8) | Potassium chloride | 0.3 |
| (9) | Panthenol dl | 0.1 |
| (10) | Citric acid | 0.1 |
| (11) | Preservative soultion (7 ppm active) | 0.2 |
| (12) | Deionized water | q.s. 100.00 |

[1]Quaternium-31 is a dialkyldimethylammonium chloride wherein each alkyl group is a saturated group consisting primarily of 16 carbon atoms and is available under the trademark ADOGEN 432 ET from Ashland Chemical Co. The Quaternium-31 of ADOGEN 432 ET is present in a solvent that contains about 13 percent ethanol and about 87 percent water.
[2]A polydimethyl cyclosiloxane tetramer having a boiling point of 176° C. sold under the designation Silicone SF-1173 by General Electric was used.
[3]Promulgen G is the designation given by Robinson-Wagner Company, Inc. for its mixture of stearyl alcohol and Ceteareth-20. Ceteareth-20 is defined in the CTFA Dictionary as the polyethylene glycol ether of Cetearyl alcohol that conforms generally to the formula $R(OCH_2 CH_2)_n OH$ where R represents a blend of cetyl and stearyl radicals and n has an average value of 20.

The conditioning emulsion was prepared by addition of the citric acid, Quaternium-31, propylene glycol and dimethylaminopropyl stearamide to the water with agitation. The resulting admixture was heated to a temperature of 145° F. with continued agitation. After a substantially homogeneous admixture was achieved, cetyl alcohol and Promulgen G were added with agitation, and the temperature of the new admixture was raised to 155° F. Agitation at 155° F. was continued for 30 minutes and the temperature of the mixture was lowered to 115° F. Potassium chloride was thereafter added with the agitation continuing until a substantially uniform admixture was obtained. Panthenol dl, the volatile cyclic silicone, perfume oil and preservative solution were then added with agitation. Agitation was continued while allowing the emulsified hair conditioning composition to cool to 90° F. at which time the composition was packaged.

Hair was treated with a composition of this Example following usual conditioning product evaluation methods. The composition provided the wet hair with a creamy feel and good combing. Combing studies (Example 2) indicated superior wet and dry combing and detangling properties were imparted to the hair by this composition.

EXAMPLE 2

Comparative, Quantitative Combing Studies

Comparative quantitative combing studies were performed using an Instron Tensile Testing apparatus (Instron Corporation, Canton, Mass.) adapted with a comb. Hair tresses were affixed to the stationary member and a comb was affixed to the moving member of the machine to provide a means for mechanical combing. Paired, standard 6 inch tresses of brown or bleached/waved hair (De Meo Brothers, New York) were used for each of the determinations. Measurements were taken of the maximum force or peak load to comb through the tress, as well as of the total energy required to comb through the tress. Peak load is the highest load in grams that was recorded during combing of the tress. Total energy is measured as the area under the load versus distance curve plotted by the instrument during a combing stroke from hair root to tip and is in units of centimeter-gram force. Of these measurements, the total energy measurement is believed to provide a more reliable indication of a composition's combing ease or detangling ability because it provides a total combing picture rather than just a portion.

In each determination, a standard amount of conditioning composition (about 0.5 milliliters) in proportion to an amount which would be used on a whole head was applied to wet, freshly shampooed hair, allowed to remain in contact with the hair for about 1 minute and then rinsed from the hair with tap water. Wet combing measurements were made directly after the rinsing step, while dry combing measurements were made after the hair had been equilibrated for about 15–24 hours in a room kept at 72° F. and 60 percent relative humidity. The first combing stroke through each tress is considered to be a measure of ease of detangling, while a subsequent combing stroke is considered to measure the conditioning properties of the composition.

The five compositions compared were as follows:

(A) A composition substantially like that of Example 1, but containing water in place of the volatile cyclic silicone, thereby simulating a commercially available hair conditioner.

(B) The composition of Example 1;

(C) The composition of Example 1 in which the volatile silicone of that composition was replaced with a volatile cyclic silicone pentamer having a boiling point of about 190°–210° C. sold under the designation Silicone SF-1202 by General Electric;

(D) The composition of Example 1 in which the volatile cyclic silicone of that composition was replaced by a non-volatile silicone (dimethylpolysiloxane) sold under the designation Silicone SF 96-50 by General Electric; and (E) The composition of Example 1 in which the volatile cyclic silicone of that composition was replaced by a very volatile silicone (hexamethyl disiloxane, boiling point 100° C.) sold under the designation Q 2 1096 by Dow Corning.

A creamy feel was noted when Compositions B and C, of this invention, were applied to wet hair. Compositions containing the very volatile and non-volatile silicones appeared and felt somewhat oily on the wet hair.

The data from each measurement of total energy or peak force required to comb through the tresses were ranked on a scale of 1 through 5; the number 1 being given to the lowest value and the number 5 being given to the highest value. The rankings were then summed over all of the eight determinations made to obtain an overall picture of the effectiveness of each composition. Thus, the lowest overall sum reflects the composition providing the best overall combing properties. The rankings and Ranking Sums are listed in Tables 1 and 2 below for total energy and peak force to comb, respectively.

TABLE 1

| | Ranking of Total Energy to Comb | | | | | | | |
|---|---|---|---|---|---|---|---|---|
| | Brown Hair | | | | Bleached/Waved Hair | | | |
| Compo- | Wet | | Dry | | Wet | | Dry | Ranking |
| sition | I* | S** | I | S | I | S | I | S | Sums |
| A | 5 | 5 | 5 | 2 | 1 | 5 | 2 | 3 | 28 |
| B | 1 | 1 | 2 | 1 | 2 | 1 | 3 | 4 | 15 |
| C | 4 | 4 | 1 | 5 | 4 | 4 | 1 | 1 | 24 |
| D | 2 | 3 | 4 | 3 | 5 | 2 | 5 | 2 | 26 |
| E | 3 | 2 | 3 | 4 | 3 | 3 | 4 | 5 | 27 |

*I = initial combing stroke, related to ease of detangling.
**S = subsequent combing stroke, related to conditioning.

TABLE 2

| | Ranking of Peak Force to Comb | | | | | | | |
|---|---|---|---|---|---|---|---|---|
| | Brown Hair | | | | Bleached/Waved Hair | | | |
| Compo- | Wet | | Dry | | Wet | | Dry | Ranking |
| sition | I* | S** | I | S | I | S | I | S | Sums |
| A | 5 | 5 | 2 | 3 | 1 | 5 | 5 | 3 | 29 |
| B | 1 | 1 | 4 | 2 | 2 | 1 | 3 | 4 | 18 |
| C | 3 | 3 | 1 | 1 | 4 | 4 | 2 | 2 | 20 |
| D | 2 | 4 | 5 | 4 | 5 | 3 | 1 | 1 | 25 |
| E | 4 | 2 | 3 | 5 | 3 | 2 | 4 | 5 | 27 |

* and **, see Table 1.

Examination of the above Tables, and particularly the Ranking Sums, demonstrates that the compositions of this invention, B and C, provided easier over-all combing than any of the other compositions studied. This superiority was found when either total energy or peak force measurements were examined.

Thus, one or the other of compositions B or C was the best in seven of the eight determinations of the total energy measurements (Table 1). In addition, hair treated with Compositions B or C required the least peak force in five of the eight determinations (Table 2).

The above results demonstrate the superior and unexpected results achieved when the volatile cyclic silicones and quaternary nitrogen-containing conditioning agents of the invention are incorporated into a particularly preferred hair conditioning composition. The compositions of this invention provide superior detangling and subsequent combing ease to wet and dry brown and bleached/waved hair compared to similar compositions containing silicones which have greater or lesser volatility (Compositions E and D, respectively), or when compared to a commercial-type conditioner which contained no silicone (Composition A). In addition, while use of the non-cyclic, but otherwise similar silicones produced oily looking and feeling conditioners, the volatile silicones useful herein provided pleasant, creamy compositions when placed on wet hair.

EXAMPLE 3

Further Comparative Quantitative Combing Studies

The efficacy of using a hair conditioning preparation of this invention was further demonstrated by a comparison of combing forces between a first composition containing only deionized water and a useful quaternary nitrogen-containing conditioning agent and a second composition of this invention containing the same two ingredients with the addition of a volatile cyclic silicone. The first composition contained 3.3 weight percent Quaternium-31 (68% active) dissolved in water. The second composition of this invention contained the same amount of Quaternium-31 with 2 weight percent Silicone SF-1173 (Example 1) replacing an equal amount of water.

Bleached/waved hair tresses were treated with either of the two compositions as is described in Example 2 with comparisons being made for both wet and dried, treated hair. Data for the peak force to comb through the tresses for the average of the first six strokes of the comb (detangling and subsequent strokes) were analyzed using a Student's t test. The reductions in force using the composition of this invention were determined to be significant at at least the 95 percent confidence level. These data are reported below in Table 3.

TABLE 3

| | Peak Force (in grams) | |
|---|---|---|
| | Wet combing Force | Dry combing Force |
| Composition 1* | 11.27 | 8.48 |
| Composition 2** | 7.55 | 6.01 |
| Percent force reduction*** | 33 | 29 |

*Composition 1 contained only deionized water and 3.3 weight percent Quaternium-31 (68% active).

The above data and reductions in peak force to comb through the tress amply illustrate the efficacy of the instant invention.

EXAMPLE 4

Conductivity Measurements

The conductivity of several compositions was measured using a conductivity bridge Model 31 or a Model 32 conductance meter with digital readout manufactured by Yellow Springs Instrument Co. The conductivity cell had a cell constant of 0.09, and measurements were taken at the concentrations noted after samples had reached thermal equilibrium at 25°-27° C.

Equivalent molar conductances were calculated at the concentrations of quaternary nitrogen-containing conditioning agent listed below using the formula:

$$\text{Equivalent Conductance} = \frac{\text{Conductivity in Micromhos}}{\text{Molar Concentration} \times 1000}$$

The molarity of the conditioner as a whole was used in the calculations.

The values for conductivity measurements on the same species varied from determination to determination. The relative magnitudes of those values within the each determination were consistant.

A. Conductivity Determination I

The data in Table 4 illustrate the effect on conductivity of a solution containing Quaternium-31 sold under the trademark ADOGEN 432 by Ashland Chemical Co. upon the addition of varying amounts of silicones. Each composition contained 3.3 weight percent ADOGEN 432 (68 percent active in a solution of approximately 13% ethanol and 87% water) to provide a 0.042 molar solution. (The molar equivalent weight for ADOGEN 432 is stated by its manufacturer to be 529 grams/mole.) The compositions so prepared had a cloudy white appearance and were of a relatively high viscosity. The silicones were added in the amounts shown in the Table and mixed by hand stirring to provide the substantially homogeneous compositions on which the measurements were made.

TABLE 4

Conductivity with Added Silicone

| Silicone Added | Amount Added (wt. %) | Equivalent Conductance |
|---|---|---|
| None | Zero | 3.8 |
| Cyclic tetramer[1] | 0.5 | 5.2 |
| Cyclic tetramer[1] | 2 | 6.2 |
| Cyclic tetramer[1] | 5 | 6.2 |
| Cyclic pentamer[2] | 2 | 5.2 |
| Linear, non-volatile[3] | 2 | 3.9 |

[1]A polydimethyl cyclosiloxane tetramer sold under the trademark Silicone SF-1173 by General Electric.
[2]A polydimethyl cyclosiloxane pentamer sold under the trademark Silicone SF-1202 by General Electric.
[3]A linear, non-volatile dimethylpolysiloxane sold under the trademark Silicone SF 96-50 by General Electric.

The results in Table 4 illustrate that addition of each of the two volatile cyclic silicones useful in this invention raised the equivalent conductance while addition of a non-volatile, linear silicone had substantially no effect upon the conductance of the solution. The results also illustrate the presence of a plateau of equivalent conductance values when between 0.5 weight percent (0.020 molar) and 2 weight percent (0.078 molar) of the tetrameric silicone was added to 0.042 molar Quaternium-31.

B. Conductivity Determination II

A series of compositions containing a constant molar amount of commercially available quaternary nitrogen-containing conditioning agent (0.042 molar) was prepared. Conductance values for each composition were measured as discussed above. Stability of the composition as to phase separation was examined approximately 24 hours after preparation of the compositions and maintenance at a temperature of about 20° to about 25° C.

The volatile cyclic silicone tetramer utilized above was then added (2 weight percent, 0.078 molar) to each composition using hand stirring to obtain a substantially homogeneous composition. Conductances of the thus prepared compositions were measured and the stability of these compositions was assessed as above. The results of determinations with and without added silicone are shown in Table 5 in which CTFA Dictionary names are utilized.

TABLE 5

Conductance and Stability

| Conditioner | Specific Conductance With No Silicone | Stability | Specific Conductance With Silicone | Stability |
|---|---|---|---|---|
| Cetrimonium chloride[1] | 32.0 | S[2] | 31.5 | U[3] |
| Steartrimonium chloride[4] | 30.8 | S | 26.3 | U |
| Tallowtrimonium chloride[5] | 33.8 | S | 30.9 | U |
| PEG-2 Cocoyl Quaternium-4 chloride[6] | 46.1 | S | 45.7 | U |
| Stearalkonium chloride[7] | 29.4 | S | 25.9 | U |
| Olealkonium chloride[8] | 31.1 | S | 31.6 | U |
| Quaternium-31[9] | 5.5 | S | 8.5 | S |
| Quaternium-18[10] | 5.4 | S | 7.1 | S |
| Quaternium-40[11,12] | — | — | — | U |
| Quaternium-41[12,13] | — | — | — | U |
| Quaternium-23[12,14] | — | — | — | U |

[1]Cetyltrimethylammonium chloride.
[2]S = Stable, No phase separation after 24 hours at about 20° to about 25° C.
[3]U = Unstable, phases separate after 24 hours at about 20° to about 25° C.
[4]Stearyltrimethylammonium chloride.
[5]Tallowtrimethylammonium chloride.
[6]A compound that conforms generally with the formula: $(R)N(CH_3)[(CH_2CH_2O)_xH][(CH_2CH_2O)_yH]^+Cl^-$ wherein R represents the coco radical and (x + y) has an average value of 2.
[7]Stearyldimethylbenzylammonium chloride.
[8]Oleyldimethylbenzylammonium chloride.
[9]See Example 1.
[10]Di-(hydrogenated tallow) dimethylammonium chloride.
[11]Poly(diallyldimethylammonium) chloride sold under the trademark MERQUAT 100 by E.M. Merck & Co.
[12]Specific conductance not calculated. Conductivity increased less than about 4% for each polymer-containing composition on addition of the volatile cyclic silicone.
[13]Copolymer of diallyldimethylammonium chloride and acrylamide sold under the trademark MERQUAT 550 by E.M. Merck & Co.
[14]A quaternary ammonium polymer formed by the reaction of dimethyl sulfate and a copolymer of N—vinylpyrrolidone and dimethylaminoethyl methacrylate sold under the trademark GAFQUAT 755 by GAF Corporation.

The above results illustrate the unique stability of the compositions of this invention as compared to compositions containing the same amounts of volatile cyclic silicone and non-useful quaternary nitrogen-containing conditioning agents 24 hours after preparation of the various compositions.

The above results also illustrate the large increase in specific conductance illustrated by the compositions of this invention as compared to same composition containing no volatile cyclic silicone. Those results further illustrate the face that little effect on conductivity occurs upon the addition of a volatile cyclic silicone to compositions containing non-useful quaternary nitrogen-containing conditioning agents.

C. Conductivity Determination III

A third conductivity determination was made to determine the effect, if any, of the inclusion of 2 weight percent iso-propanol on the conductivity of compositions containing a quaternary nitrogen-containing agent alone and with two weight percent added volatile cyclic silicone tetramer. The results of these measurements showed differences in values for specific conductances compared to compositions containing no iso-propanol. However, the large increases in specific conductance for the compositions of this invention were still present, while smaller increases and decreases were noted for compositions that contained iso-propanol, volatile cyclic silicone and non-useful quaternary nitrogen-containing conditioning agent.

Examination of all of the above determinations indicates the following: (1) the compositions of this invention behave differently from compositions containing either different silicones or different quaternary compounds, as shown by stability and conductivity measurements; (2) an interaction or complex formation between the volatile cyclic silicone and the useful quaternary nitrogen-containing conditioning agent occurs; and (3) the interaction reaches a maximum at a silicone-to-cationic compound molar ratio between about 0.5:1 and about 2:1.

EXAMPLE 5

C$^{13}$ Nuclear Magnetic Resonance Measurements

C$^{13}$ Nuclear magnetic resonance (NMR) measurements of a 10 weight percent solution of ADOGEN 432 in water showed the peak for the methylene carbon adjacent to the quaternary nitrogen atom (1-carbon) to resonate at 63.18 ppm downfield from the external standard. The spectrum for the same composition to which 2 percent of a volatile cyclic silicone tetramer was added showed that the same 1-carbon atom peak occurred at 61.15 ppm downfield from the standard, an upfield shift of about 2 ppm. The difficulty-assignable remaining peaks attributable to the carbon atoms on the long chain aliphatic groups shift downfield on addition of the silicone.

These results are consistent with the results of Mazda et al., *Journal of Colloid and Interfacial Science*, 76(2), 532–540 (1980) wherein C$^{13}$ NMR spectra of lauryldimethylammonium chloride were reported. There, the similar upfield shift of the 1-carbon on increasing concentration was interpreted as a change from a substantially dispersed composition to one in which micelles were formed, and was used to accurately calculate the critical micelle concentration.

Here, it is thought that the complexing interaction between the silicone and conditioner may result in smaller or more micelles being formed. That interpretation would be in line with the observed increases in conductivity observed which could result from an increase in mobility within the compositions of this invention caused by the formation of more or smaller micelles.

EXAMPLE 6

Hair Combing Studies

Further mechanical hair combing studies using the Instron apparatus were conducted in a manner substantially identical to that disclosed in Example 2. Normal brown hair or bleached/waved hair tresses were again used and combing was done on both wet and dry hair.

The data presented below are for wet combing of bleached/waved hair, the type of hair that normally requires a conditioning agent, and the type of hair for which differences in magnitude of effect were most noted. No differences, statistically significant at at least the 90 percent confidence level, were noted for dry combing. Differences, statistically significant at at least the 90 percent confidence level, were noted for wet combing on normal brown hair. Those results are shown in Table 7 of this Example.

Five quaternary nitrogen-containing conditioning agents were used in these determinations, each at a concentration of 0.042 molar in water, along with the volatile cyclic silicone tetramer (Example 1) present at 0.078 molar. The quaternary nitrogen-containing conditioning agent used in each of the compositions of this combing test are as follows:

| Composition | Conditioner |
|---|---|
| F | Quaternium-31 (ADOGEN CG, in which iso-propanol replaced the ethanol present in ADOGEN ET of Example 1) |
| G | Di-(hydrogenated tallow) dimethylammonium chloride |
| H | Stearldimethylbenzyl-ammonium chloride |
| I | Oleyldimethylbenzyl-ammonium chloride |
| J | Tridecylmethylammonium chloride |

Mean peak load (gram force) data for mechanically combing bleached/wound hair treated with Compositions F–J are shown in Table 6, below. Each of Compositions F–I provided wet combing that was superior to all of the compositions listed below it in Table 6 at a confidence level of at least 97.5 percent. Lower mean peak load values indicate better combing.

TABLE 6

Mean Peak Combing Load

| Composition | Mean Peak Load | Standard Deviation |
|---|---|---|
| F | 5.216 | 1.656 |
| G | 7.574 | 1.458 |
| H | 14.810 | 4.332 |
| I | 21.000 | 6.192 |
| J | 30.980 | 12.090 |

Peak load and total energy data showed Compositions F and G to provide superior combing at at least the 95 percent confidence level compared to the same compositions without the volatile cyclic silicone. When similar comparisons were made, using the conditioners of Compositions H, I and J, the peak load was reduced, but the reductions in peak load were not significant at the 90 percent confidence level or better. Total energies were also not significantly lower at the 90 percent confidence level for Compositions H and J when compared to compositions containing no volatile silicone. There was a significant decrease in total energy in this comparison with the conditioner of Composition I.

An apparently anomalous behaviour was noted for a composition similar to F in which ADOGEN ET (Example 1) was used rather than the ADOGEN CG. There, the peak load and total energy values for the silicone-ADOGEN ET composition were lower than those for the silicone-ADOGEN CG Composition (F), but the improvement in combing when compared to use of a composition containing ADOGEN ET alone in water was not great enough to be significant at a 90 percent confidence level or greater. It is believed that the reason for the statistical insignificance of the improvement stems from the relatively small peak load and total energy values without volatile cyclic silicone present and the magnitude of the standard deviation in the data. The composition containing ADOGEN ET and the volatile cyclic silicone provided peak load values that were an improvement over those with Compositions G–J at a confidence level of at least 99.5. There was no significant difference over the peak load value for Composition F that contained ADOGEN CG, as was expected.

Ranking compositions F–J (1–5, 1 being best) for their combined effects on mean peak load determined from mechanically wet combing both bleached/waved and normal hair provides the data shown in Table 7, below. The sums of the rankings are shown in the right-hand column.

TABLE 7

| Composition | Bleached/Waved Hair | Normal Hair | Ranking Sums |
|---|---|---|---|
| F | 1 | 2 | 3 |
| G | 2 | 1 | 3 |
| H | 3 | 3 | 6 |
| I | 4 | 4 | 8 |
| J | 5 | — | — |

The above peak load data, rankings and ranking sums again illustrate the superiority of the compositions of this invention (F and G) over similar compositions containing the same amounts of a volatile cyclic silicone and a non-useful cationic conditioner. It is also noted that only the useful compositions of this invention showed both a stability from phase separation 24 hours after preparation and a large increase in conductivity on preparation compared to the conductivity of a composition of the cationic conditioner with no added volatile cyclic silicone.

The present invention has been described with respect to the preferred embodiments of the invention. It will be clear to those skilled in the art that modifications and/or variations of the compositions can be made without departing from the scope of the invention set forth herein. The invention is defined by the claims which follow.

What is claimed is:

1. A hair conditioning composition comprising an emulsion of water, about 1 to about 4 percent by weight of a polydimethyl cyclosiloxane having an average of about 3 to about 6 —[O—Si(CH$_3$)$_2$]-units and having an atmospheric boiling point of from about 150° C. to about 250° C., from about 0.5 to about 5 weight percent of a quaternary nitrogen-containing conditioning agent having two long aliphatic chains each of which contains about 12 to about 18 carbons and two short chain alkyl groups having one or two carbons each bonded to the quaternary nitrogen, from about 0.5 to about 10 weight percent of a long chain fatty alcohol having about 11 to about 18 carbons in said long chain, and about from 0.1 to about 2 weight percent of a tertiary amidoamine having a structure conforming to the formula R$^1$—C(=O)—NH—R$^2$—N(R$^3$)$_2$ wherein R$^1$ is a fatty chain having about 11 to about 17 carbon atoms, R$^2$ is an alkylene group having 2 or 3 carbon atoms and each R$^3$ is ethyl or methyl, said polydimethyl cyclosiloxane and said quaternary nitrogen-containing conditioning agent being present in said composition in a molar ratio between about 0.5:1 to 2 to 1 and said quaternary conditioning agent being the sole quaternary compound in the composition.

2. The hair conditioning composition according to claim 1 wherein said long chain fatty alcohol is present at about 2 to about 5 weight percent of said composition.

3. The hair conditioning composition according to claim 1 wherein said tertiary amidoamine is present at about 0.25 to about 1 weight percent of said composition.

4. A hair conditioning composition comprising an emulsion including at least about 80 weight percent water, from about 1.5 to about 3 weight percent polydimethyl cyclosiloxane having an average of about 3 to about 6—[O—Si(CH$_3$)$_2$]-units and having an atmospheric boiling point of about 170° C. to about 220° C., from about 2 to about 3 weight percent of a conditioning agent containing one quaternized nitrogen atom having two long aliphatic chains each having about 12 to about 18 carbon atoms and two short chain alkyl groups having one or two carbon atoms each bonded to the quaternary nitrogen, from about 2 to about 5 weight percent of a long chain fatty alcohol having about 11 to about 18 carbon atoms in said long chain, and from about 0.25 to about 1 weight percent of a tertiary amidoamine having a structure conforming to the formula R$^1$—C(=O)—NH—R$^2$—N(R$^3$)$_2$ wherein R$^1$ is a fatty chain having about 11 to about 17 carbon atoms, R$^2$ is an alkylene group having 2 or 3 carbon atoms and each R$^3$ is ethyl or methyl, said polydimethyl cyclosiloxane and said quaternary nitrogen-containing conditioning agent being present in said composition in a molar ratio between about 0.5:1 to 2 to 1 and said quaternary conditioning agent being the sole quaternary compound in the composition, and wherein said polymethyldimethyl cyclosiloxane and said quaternary nitrogen-containing conditioning agent form a complex within said water.

5. The hair conditioning composition according to claim 4 wherein said tertiary amidoamine is dimethylaminopropyl stearamide or diethylaminoethyl stearamide.

6. The hair conditioning composition according to claim 4 wherein said long chain fatty alcohol is selected from the group consisting of cetyl alcohol, stearyl alcohol and mixtures thereof.

7. A hair conditioning composition comprising water, a polydimethyl cyclosiloxane having an average of about 3 to about 6—[O—Si(CH$_3$)$_2$]-units and having an atmospheric boiling point of about 150° C. to about 250° C. present at about 1 to about 4 percent by weight of said composition, and a quaternary nitrogen-containing conditioning agent having two long chains each of which contains about 12 to about 18 carbon, atoms and two short chain alkyl groups having one or two carbon atoms each bonded to said quaternary nitrogen, said polydimethyl cyclosiloxane and said quaternary nitrogen-containing conditioning agent being present in said composition in a molar ratio between about 0.5:1 to 2 to 1 and said quaternary conditioning agent being the sole quaternary compound in the composition.

8. The hair conditioning composition according to claim 7 wherein said quaternary nitrogen-containing conditioning agent is selected from the group consisting of distearyldimethylammonium chloride, dilauryldimethylammonium chloride, dimethyldi-(hydrogenated tallow)ammonium chloride and dialkyldimethylammonium chloride wherein each of said alkyl groups is a saturated group consisting primarily of 16 carbon atoms.

9. The conditioning composition according to claim 7 wherein said polydimethyl cyclosiloxane is present at about 1.5 to about 3 percent by weight of said composition, and boils at from about 170° C. to about 220° C.

10. The conditioning composition according to claim 7 in the form of an emulsion having water as the external phase.

11. The conditioning composition according to claim 10 additionally containing about 0.5 to about 10 weight percent of a long chain fatty alcohol having about 11 to about 18 carbon atoms in said long chain.

12. The conditioning composition according to claim 11 additionally containing from about 0.25 to about 1 weight percent of a tertiary amidoamine having a structure conforming to the formula R$^1$—C(=O)—NH—R-

$-N(R^3)_2$ wherein $R^1$ is a fatty chain having about 11 to about 17 carbon atoms, $R^2$ is an alkylene group having 2 or 3 carbon atoms and each $R^3$ is ethyl or methyl.

13. The conditioning composition according to claim 7 wherein said polydimethyl cyclosiloxane and said quaternary nitrogen-containing conditioning agent form a complex within said water.

14. The hair conditioning composition according to claim 13 wherein said water comprises at least about 80 weight percent of said composition.

15. The hair conditioning composition according to claim 13 wherein said polydimethyl polysiloxane boils at a temperature of from about 170° C. to about 220° C. at atmospheric pressure.

16. The hair conditioning composition according to claim 13 wherein said polydimethyl cyclosiloxane is present at about 1.5 to about 3 percent by weight of said composition.

17. The hair conditioning composition according to claim 13 wherein said quaternary nitrogen-containing conditioning agent is selected from the group consisting of distearyldimethylammonium chloride, dilauryldimethylammonium chloride, dimethyldi-(hydrogenated tallow)ammonium chloride and dialkyldimethylammonium chloride wherein each of said alkyl groups is a saturated group consisting primarily of 16 carbon atoms.

18. The hair conditioning composition according to claim 13 wherein said quaternary nitrogen-containing conditioning agent is present at about 2 to about 3 percent by weight of the composition.

19. A method of conditioning damaged hair which comprises contacting said hair with the composition of claim 1.

20. A method of conditioning damaged hair which comprises contacting said hair with the composition of claim 1.

* * * * *

UNITED STATES PATENT AND TRADEMARK OFFICE
CERTIFICATE OF CORRECTION

PATENT NO. : 4,777,037

DATED : October 11, 1988

INVENTOR(S) : Wagman et al.

It is certified that error appears in the above-identified patent and that said Letters Patent is hereby corrected as shown below:

Column 3, Line 26, "hari sprays" should read --hair sprays--

Column 6, Line 57, "existance" should read --existence--

Column 13, Line 14, "difficulty" should read --difficultly--

Column 18, Line 19, Claim 20, "Claim 1" should read --Claim 7--.

Signed and Sealed this

Twenty-seventh Day of June, 1989

Attest:

DONALD J. QUIGG

*Attesting Officer*  *Commissioner of Patents and Trademarks*